(12) United States Patent
Parasco et al.

(10) Patent No.: US 11,717,634 B2
(45) Date of Patent: Aug. 8, 2023

(54) THERAPEUTIC OXYGEN BREATHING APPARATUS AND EXERCISE SYSTEM

(71) Applicant: MaxxO2, LLC., Austin, TX (US)

(72) Inventors: Anthony Lee Parasco, Bradenton, FL (US); Milton Verret, Austin, TX (US)

(73) Assignee: MAXXO2, LLC, Austin, TX (US)

( * ) Notice: Subject to any disclaimer, the term of this patent is extended or adjusted under 35 U.S.C. 154(b) by 420 days.

(21) Appl. No.: 16/832,172

(22) Filed: Mar. 27, 2020

(65) Prior Publication Data

US 2020/0261683 A1     Aug. 20, 2020

Related U.S. Application Data (63) Continuation-in-part of application No. 16/590,864, filed on Oct. 2, 2019.
(Continued)

(51) Int. Cl.
*A61M 16/10* (2006.01)
*A61M 16/06* (2006.01)
(Continued)

(52) U.S. Cl.
CPC .... *A61M 16/1005* (2014.02); *A61M 16/0075* (2013.01); *A61M 16/06* (2013.01);
(Continued)

(58) Field of Classification Search
CPC .............. A61M 16/00; A61M 16/0057; A61M 16/0075; A61M 16/0078; A61M 16/0081;
(Continued)

(56) References Cited

U.S. PATENT DOCUMENTS

| 1,044,031 A | 11/1912 | Drager |
|---|---|---|
| 1,144,812 A | 6/1915 | Claren |

(Continued)

FOREIGN PATENT DOCUMENTS

| EP | 0744184 A1 | 11/1996 |
|---|---|---|
| EP | 1721629 A1 | 11/2006 |

(Continued)

OTHER PUBLICATIONS

International Search Report and Written Opinion of ISA of PCT Application No. PCT/US2020/025137, dated Dec. 9, 2020.

*Primary Examiner* — Joseph D. Boecker
(74) *Attorney, Agent, or Firm* — Amster Rothstein & Ebenstein LLP (57) ABSTRACT

An exercise with oxygen therapy (EWOT) apparatus for rejuvenating oxygen-depleted cell tissue and simulating high altitude oxygen conditions. The EWOT apparatus includes a first cylindrical bladder for providing oxygen-enriched air and a second bladder for providing lower-purity hypoxic air. The first bladder is retained within an open, lightweight rectangular-shaped frame having vertical frame members. An air supply source provides the oxygen-enriched and hypoxic air to the first and second bladders, respectively. A control switch, which can be manually and/or programmed to automatically operate, selectively delivers the oxygen-enriched and/or hypoxic air to a breathing mask worn by a user while exercising on exercise equipment. The first bladder includes a plurality of weights which provide a positive pressure to the air therein. The cylindrical first bladder is attached to the vertical frame members with slidable rings and expands and collapses in a vertical direction when being filled or during use, respectively.

28 Claims, 7 Drawing Sheets

Related U.S. Application Data (60) Provisional application No. 62/740,287, filed on Oct. 2, 2018.

(51) Int. Cl.
*A61M 16/20* (2006.01)
*A61M 16/00* (2006.01)
*A63B 24/00* (2006.01)
*A61M 16/12* (2006.01)
*A63B 23/18* (2006.01)

(52) U.S. Cl.
CPC .......... *A61M 16/12* (2013.01); *A61M 16/122* (2014.02); *A61M 16/201* (2014.02); *A61M 16/202* (2014.02); *A63B 23/18* (2013.01); *A63B 24/0062* (2013.01); *A61M 16/0078* (2013.01); *A61M 2205/3303* (2013.01); *A61M 2209/08* (2013.01); *A63B 2213/006* (2013.01); *A63B 2225/62* (2013.01)

(58) Field of Classification Search
CPC .. A61M 16/0084; A61M 16/10; A61M 16/12; A61M 16/122; A61M 16/201; A63B 23/18; A63B 2213/005; A63B 2213/006; A63B 24/0062
See application file for complete search history.

(56) References Cited

U.S. PATENT DOCUMENTS

| | | | |
|---|---|---|---|
| 2,042,474 A | 6/1936 | McKesson | |
| 2,880,719 A | 4/1959 | Andersen | |
| 2,969,789 A * | 1/1961 | Morch | A61M 16/00 128/205.24 |
| 3,046,979 A * | 7/1962 | Andreasen | A61M 16/0009 128/205.16 |
| 3,441,020 A | 4/1969 | Wortz et al. | |
| 2,217,575 A | 10/1970 | von Hoff | |
| 4,086,923 A | 5/1978 | Henkin | |
| 4,121,578 A | 10/1978 | Torzala | |
| 4,210,137 A | 7/1980 | Henkin | |
| 4,427,056 A | 1/1984 | Johnson et al. | |
| 5,207,623 A | 5/1993 | Tkatchouk et al. | |
| 5,261,457 A | 11/1993 | Zapata et al. | |
| 5,850,833 A | 12/1998 | Kotliar | |
| 5,924,419 A | 7/1999 | Kotliar | |
| 6,634,355 B2 | 10/2003 | Colas | |
| 6,718,980 B2 | 4/2004 | Carter | |
| 6,799,570 B2 | 10/2004 | Fisher et al. | |
| 6,871,645 B2 | 3/2005 | Wartman et al. | |
| 6,962,154 B2 | 11/2005 | Krebs | |
| 7,100,606 B2 | 9/2006 | Fisher et al. | |
| 7,578,293 B2 | 8/2009 | Matthiessen et al. | |
| 7,681,573 B2 | 3/2010 | Matthiessen et al. | |
| 7,955,294 B2 | 6/2011 | Stenzler et al. | |
| 8,118,713 B2 | 2/2012 | Foley et al. | |
| 8,161,966 B2 | 4/2012 | Foley et al. | |
| 8,475,340 B2 | 7/2013 | Maybaum | |
| 8,663,069 B2 | 3/2014 | Foley et al. | |
| 8,758,202 B2 | 6/2014 | Foley et al. | |
| 9,649,460 B2 | 5/2017 | Robitaille et al. | |
| 9,833,643 B2 | 12/2017 | Squibb | |
| 9,987,447 B2 | 6/2018 | Robitaille et al. | |
| 2003/0145853 A1 | 8/2003 | Muellner | |
| 2003/0172929 A1 | 9/2003 | Muellner | |
| 2006/0144396 A1 | 7/2006 | DeVries et al. | |
| 2006/0185669 A1 | 8/2006 | Bassovitch | |
| 2009/0173348 A1 | 7/2009 | Fisher et al. | |
| 2013/0139819 A1 * | 6/2013 | Chervin | A61M 16/0072 128/205.16 |
| 2014/0041662 A1 | 2/2014 | Almqvist | |
| 2014/0261406 A1 | 9/2014 | Fabian | |
| 2015/0007819 A1 | 1/2015 | Maconaughay et al. | |
| 2015/0011363 A1 | 1/2015 | Foley et al. | |
| 2015/0031506 A1 | 1/2015 | Foley et al. | |
| 2015/0314145 A1 * | 11/2015 | Squibb | A62B 9/02 128/204.21 |
| 2018/0193583 A1 * | 7/2018 | Anderson | A63B 23/18 |
| 2019/0126096 A1 * | 5/2019 | Squibb | A61M 16/201 |

FOREIGN PATENT DOCUMENTS

| | | |
|---|---|---|
| WO | 2000010632 A1 | 3/2000 |
| WO | 2007004903 A2 | 1/2007 |

\* cited by examiner

THERAPEUTIC OXYGEN BREATHING APPARATUS AND EXERCISE SYSTEM

CROSS REFERENCE TO RELATED APPLICATIONS

This patent application is a Continuation-in-Part of U.S. patent application Ser. No. 16/590,864, filed Oct. 2, 2019, which claims the benefit of U.S. Provisional Application Ser. No. 62/740,287, filed Oct. 2, 2018, the contents of which are incorporated by reference herein in their entireties.

BACKGROUND OF THE INVENTION

1. Field of the Invention

The present invention relates to an exercise with oxygen therapy apparatus for selectively providing inhalation-air to a user during and after exercising from first and second inflatable bladders containing different oxygen levels with respect to ambient oxygen at sea level.

2. Description of the Prior Art

Therapeutic breathing techniques and devices, such as exercise with oxygen therapy (EWOT) are often prescribed by physicians to patients requiring aerobic physical therapy. Athletes have also found EWOT to be helpful for altitude training or extending the duration of an aerobic exercise activity. EWOT has been found to increase recovery time from muscle fatigue during exercise, as well as treating stress conditions that cause inflammation of cell tissue, for example, by reducing arterial inflammation associated with reduced oxygen levels which can occur during extensive physical activity.

Currently, most EWOT devices are crude and cumbersome devices that occupy a significant amount of floor and wall space. Although some EWOT devices could be made with a smaller footprint, many of these devices are not easily transportable and/or storable. Once these EWOT devices are assembled and in place, it can be difficult to transport the devices without completely dismantling them. Additionally, the prior art EWOT devices do not maintain a positive air pressure upon the air bladders that store and provide oxygen or other similar gases to the user during a therapeutic exercise routine. Also, most EWOT devices only supply a single air source (e.g., higher purity oxygen or lower purity hypoxic oxygen), without ability for multiple air sources to be used with the same EWOT device. Other EWOT devices which operate with multiple air sources have other notable deficiencies and are of need for improvement.

For example, U.S. Pat. No. 9,833,643 discloses a dual compartment air-reservoir that selectively provides, via a mechanical control switch, high or low levels of oxygenated air to a user while exercising and wearing a breathing mask. More specifically, the '643 patent discloses a first air-reservoir that stores a first concentration of inhalation-air at ambient pressure (e.g., 93% oxygen), a second air-reservoir that stores a second concentration of inhalation-air at ambient pressure (e.g., 10% oxygen). The '643 patent discloses a single rectangular-shaped plastic bag which is hung directly from a wall or from a stand-alone frame. The bag is partitioned by stitching of the plastic material to form two separate air-reservoirs or bladders. The '643 patent includes air reservoirs or bladders which are not air-tight or protected internally with a medical grade coating to prevent contamination of the air inside. The reservoirs cannot hold air for more than a few minutes without deflating. A commercially available oxygen concentrator is connected to both bladders by separate air hoses connected to inlets of the first and second bladders. The oxygen concentrator pumps each bladder with the predetermined highly oxygenated and low (hypoxic level) percentage of oxygen at ambient pressure. A single control switch is coupled to inlets of each bladder via separate air tubing. The control switch includes a manually operated actuator which allows the user to select and pass through the oxygenated air flow from one of the bladders at a time to the breathing mask as the user exercises (e.g., riding a stationary bicycle, running on a treadmill, etc.).

During an aerobic exercise routine, such as pedaling a stationary bicycle or running on a treadmill, the user will eventually diminish the oxygen levels in the tissue cells as lactic acid increases. As the user's demand for oxygen increases and the user will experience heavier breathing and increased heart rate, which result from trying to provide more oxygen from the lungs and through the vascular system to the tissue cells demanding greater amounts of oxygen to reduce the lactic acid. As well, when the cell tissue oxygen levels are low or depleted for prolonged periods, temporary inflammation can occur in the linings of the blood vessels, which further deprives oxygen to the oxygen-depleted cell tissues.

EWOT can help address such physical distress conditions associated with reduced levels of oxygen while exercising by receiving high concentrations of oxygen for a predetermined time, e.g., 15 minutes. Exercise training while breathing a high concentration of oxygen has been found to help prolong the exercise activity by diminishing lactic acid buildup and, over time, can increase the user's endurance because sufficient amounts of oxygen are constantly being supplied to the user while exercising. It has also been known to improve or help numerous medical conditions or ailments including, for example, Lyme disease, dementia/Alzheimer and blood clots.

EWOT can also be used to train for physical stress conditions associated with physical activities occurring at high altitudes (e.g., greater than 600 meters above sea level). Generally, a user training with EWOT can improve his/her endurance while exercising by breathing alternative air flows, i.e., switching back and forth for predetermined durations, between a lower (hypoxic) level of oxygen to simulate high altitude conditions and a highly oxygenated air to replenish oxygen depleted cell tissue. The low concentration of oxygen (e.g., 8% to 20.95% oxygen) stored in the other bladder can be used to breathe while exercising for a predetermined time to thereby simulate and train the user's body to adapt to low oxygen conditions which naturally occur at high altitudes. When a person is physically active while subjected to high altitude conditions, cell tissue can quickly burn through the low levels of oxygen breathed through the air. Extended periods of low levels of oxygen can lead to well-known hypoxic conditions in which the person can exhibit symptoms such as, for example, shortness of breath, nausea, light-headedness or dizziness, headaches, fatigue, etc. To help address these undesirable medical conditions, prescribed training with EWOT can help cause vasodilation of the micro vessels and capillaries in the body of a user. In particular, exercising with EWOT can help reduce inflammation of the inner cell wall linings of the vessels, thereby allowing the blood vessels to expand so that the muscles, organs and other cell tissues can quickly be refreshed with new and a plentiful flow of red blood cells that is enriched with higher-than-normal levels of oxygen purity during and after completion of an EWOT exercise routine.

The EWOT apparatus and system described in the '643 patent and other prior art has a number of drawbacks. For example, the bladder that stores the high concentration of oxygenated air at ambient pressure will require the user to breathe harder to draw the oxygen enriched air through the air tubes and the control switch, and eventually to the breathing mask. That is, the lack of positive pressure in the air results in a slower delivery of oxygen to the user's oxygen-depleted cell tissue. Another drawback is that the user must manually initiate the switching of the control switch to deliver either the high or low concentration of oxygen through the mask for breathing. Manual switching between oxygen sources can be considered an interruption in the exercise routine for some users. Yet another drawback is that the air-reservoir bag is large and generally flat and is hung from a wall or a stand which requires a large footprint (e.g., having a width of at least 5 feet and a height of at least 6 feet) during use. Still another drawback is that the bladder of the '643 patent is not leak-proof, which means that the exerciser must use the system immediately or very soon after filling the bladder with the desired oxygen, thereby making it difficult, if not impossible to set-up the system beforehand. In addition to higher concentrated oxygen constantly escaping the bladder via leakage, ambient air can also enter the bladder, thereby diluting the desired/predetermined purer levels of oxygen. As well, because the inside of the '643 bladder is not medically treated or coated, it is possible that the air can become contaminated, tainted and/or diluted of its purity.

Therefore, it is desirable to provide an exercise with oxygen therapy apparatus which is capable of providing a selected concentration of oxygenated air at a positive pressure to the user. It is further desirable to provide an EWOT system having a leak-proof bladder that does not allow the contents to randomly and uncontrollably escape, as well as provide a medical grade coating in the interior of the bladder to prevent contaminants from mixing with the desired concentration of oxygen. It is also desirable to provide an EWOT system with an airflow controller which includes programming for selecting various modes of automated operation, as well receive feedback from one or more electronic sensors to provide automated adjustments during selected training routines. Moreover, is desirable to provide an EWOT system that has a reduced footprint to free up wall/floor space and enable use in smaller or confined spaces.

The novel features of the present invention, which are considered as characteristic of the invention, are set forth in the appended claims. The invention itself, however, both as to its construction and its mode(s) of operation, together with additional advantages and objects, will be best understood from the following detailed description of a preferred embodiment, when read with reference to the accompanying drawings.

SUMMARY OF THE INVENTION

In accordance with the embodiments of the invention described herein, the deficiencies of the prior art are overcome by an exercise with oxygen therapy apparatus for selectively providing positive pressure inhalation-air to a user during and after exercising from first and second inflatable bladders having oxygen levels above and below ambient oxygen at sea level.

The various embodiments of the present invention have been shown to increase energy, aid recovery, boost stamina and build immunity for both professional and amateur athletes alike. It has also been reported to have helped aid patients with a variety of health conditions and ailments.

In one embodiment, a therapeutic oxygen breathing apparatus comprises: an air reservoir having a first bladder and a second bladder, the first and second bladders being configured for storing air having different percentages of oxygen therein; a frame structure configured to support at least the first bladder in a vertical direction; a weighted member attached to and positioned proximate an upper portion of the first bladder, the weighted member having sufficient weight to apply a downward force on the first bladder when filled with air, such that a constant, predetermined positive pressure is applied to the air stored within the first bladder; wherein the first bladder includes a first inlet for receiving a first quantity of air having a first concentration of oxygen and the second bladder includes a second inlet for receiving a second quantity of air having a second concentration of oxygen; and wherein the first bladder includes a first outlet for releasing a first portion of stored air having the first concentration of oxygen and the second bladder includes a second outlet for releasing a second portion of stored air having the second concentration of oxygen.

In one aspect, the first and second bladders are physically separated. In another aspect, the second bladder is attached to the first bladder.

In one aspect, the first concentration of oxygen is greater than ambient air concentration of oxygen. In another aspect, the first concentration of oxygen is greater than ninety percent. In yet another aspect, the second concentration of oxygen is less than ambient air concentration of oxygen. In still another aspect, the second concentration of oxygen is between 8% to 20.95%.

In one aspect, the first container is cylindrical. In another aspect, the frame includes a plurality of vertical and horizontal frame members collectively arranged in a rectangular shape, wherein the frame has a height-to-width ratio greater than one. In yet another aspect, the first bladder is positioned within the rectangular frame in a vertical direction and slidably attached to the vertical frame members. In still another aspect, the first bladder is attached to the vertical frame members via a plurality of rings.

In one aspect, the weighted member is attached to an exterior portion of the first bladder and slidably moves along one of the vertical frame members. In another aspect, the weighted member is positioned on an upper surface portion of the first bladder.

In one aspect, the first outlet is in fluid communication with a first airflow directional valve that permits unidirectional airflow out of the second bladder. In another aspect, the second outlet is in fluid communication with a second airflow directional valve that permits unidirectional airflow of air out of the second bladder. In still another aspect, the second bladder is attached to the frame.

In one aspect, the therapeutic oxygen breathing apparatus further comprises a breathing mask having an inlet which is coupled to the first and second bladders via a control switch. In another aspect, the control switch is in fluid communication with the first and second outlets of the first and second bladders. In yet another aspect, the control switch includes a valve and actuator for manually selecting airflow from at least one of the first and second bladders to the breathing mask. In still another aspect, the control switch includes a programmable microcontroller for executing routines which automatically control a valve to selectively permit air to flow from at least one of the first and second bladders to the breathing mask. In another aspect, the control switch is configured to receive electronic signals from one or more biometric sensors in communication with a user wearing the breathing mask. In yet another aspect, the control switch includes programming that sends electronic signals to actuate the valve which adjusts, in real time, air flow from at least one of the first and second bladders, in response to the electronic signals from the one or more sensors. In a further aspect, the control switch includes a first control switch for receiving airflow from the first bladder and a second control switch for receiving airflow from the second bladder. In still another aspect, the first and second control switches are in electronic communication with each other.

In another embodiment, a dual bladder system for supplying gasses while exercising, comprises: a cylindrical inflatable and collapsible first bladder dimensioned and configured to receive a first gas; a second bladder dimensioned and configured to receive a second gas; and a mixer coupled to the first and second bladders, the mixer having an actuator for selectively providing at least one of the first and second gases to a user.

In one aspect, the first gas and the second gas contain different percentages of oxygen. In another aspect, the dual bladder system further comprises a frame structure configured to support at least the first bladder in a vertical direction.

In one aspect, the first bladder is pleated such that the pleats unfold to permit the first bladder to expand during receipt of the first gas. In another aspect, the pleats are biased to return to a folded state and collapse the first bladder in a vertical direction as the first gas is depleted from the first bladder.

BRIEF DESCRIPTION OF THE DRAWINGS

The invention will be further described below with reference to the drawings in which.

To facilitate an understanding of the invention, identical numerals have been used, when appropriate, to designate the same or similar elements that are common to all of the figures. Further, unless stated otherwise, the features shown in the figures are not drawn to scale, but are shown for illustrative purposes only.

DETAILED DESCRIPTION OF THE PREFERRED EMBODIMENTS

Figure 1:
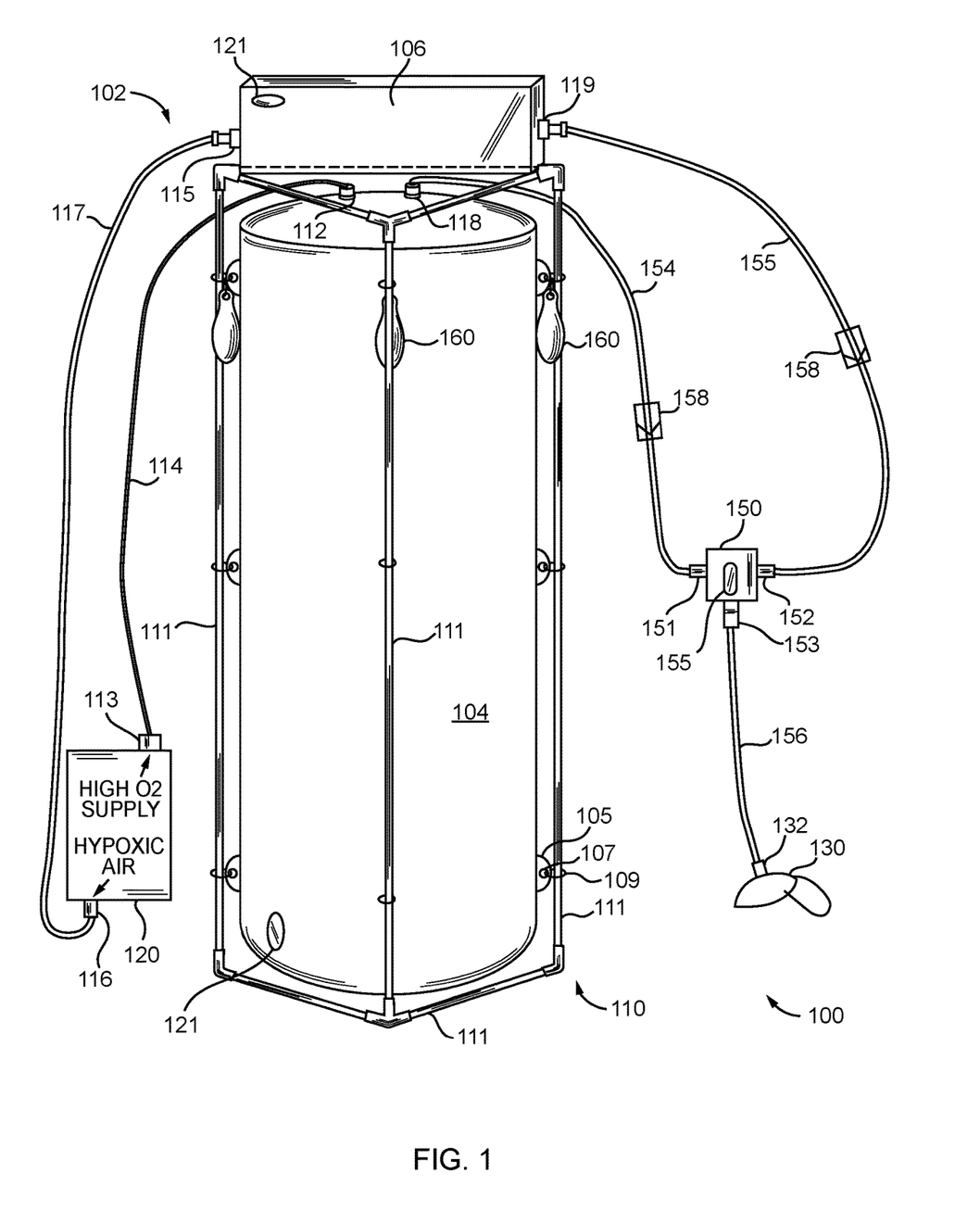
FIG. 1 is a top, front, right-side perspective view of an embodiment of an exercise with oxygen therapy (EWOT) training device having a support frame, a first inflatable bladder, a second inflatable bladder, a support frame, an air supply and a first airflow control system according to the present invention for use with an exercise device.

Referring now to FIG. 1, a first embodiment of an exercise with oxygen therapy (EWOT) apparatus 100 is illustratively shown. The EWOT apparatus 100 includes an air reservoir 102 having a first bladder 104, a second bladder 106, an air supply 120 for providing a plurality of predetermined concentrations of air e.g., a high level of oxygen to the first bladder 104 and a low (hypoxic) adjustable level of oxygen to the second bladder 106, a support structure or frame 110 for securing the first and second bladders 104, 106, a breathing mask 130 which is worn by a user when exercising on exercise equipment, such as a stationary bicycle, treadmill, and the like, and a control switch 150 for switching between and passing the high and/or low airflow concentrations from each bladder 104, 106 to the mask 130 so the user can selectively breathe the oxygen-enriched air or the hypoxic air while exercising. Although the present embodiments are discussed in terms of a breathing mask 130, such breathing apparatus is not considered limiting as other well-known breathing devices can be used such as, for example, a nasal cannula, a breathing tube and/or other well-known breathing devices that enable a user to breathe through the nose and/or mouth. Preferably, the predetermined concentration of air being delivered to the first bladder 104, via the air supply 120, includes oxygen that is above 20.95% oxygen at sea level, although such high oxygen concentration and simulated altitude levels are not considered limiting. Preferably, the predetermined concentration of air being delivered to the second bladder 106, via the air supply 120, includes an adjustable low level of oxygen that is illustratively between 8% and 20.95% at sea level, which can simulate altitude levels up to 21,000 feet, although such low oxygen concentration and simulated altitude levels are not considered limiting. The oxygen enriched air helps to quickly supply oxygen to the oxygen-depleted cell tissues and thereby allows the user to exercise for longer periods of time. Alternatively, the user can breathe the hypoxic air while exercising to simulate and train for high altitude breathing conditions. Breathing the hypoxic air causes the body's micro vessels and capillaries to open even wider, or vasodilate even more so, thereby increasing the exerciser's body need and reception of even more healthy red blood cells than when the user is breathing the highly oxygenated air. It has been reported that breathing hypoxic air over long periods of time without replenishing the body with fresh or high purity oxygen can cause inflammation in the inner wall linings of the microvessels and capillaries, thereby making the microvessels shrink in diameter, i.e., constrict and reducing blood flow to the cell tissue. However, it has also been found that inhaling hypoxic air for shorter periods such as while training with an EWOT system has an opposite effect on the body. In particular, when participating in EWOT, the hypoxic air is used solely as a way to "starve" the body of oxygen for a very limited time (e.g., seconds or a few minutes) so that the body's microvessels and capillaries dilate. Once the blood vessels are dilated from the hypoxic air, the user switches over to and breathes the highly oxygenated air, which quickly delivers the oxygen enriched air to the oxygen deprived cell tissues, thereby enhancing quick recovery of the cell tissues during the exercise routine. A pioneer in the study of EWOT was Dr. Manfred Von Ardenne, who spent years conducting studies on how the body functions with and responds to increased levels of oxygen, also known as oxygen saturation. For a detailed understanding of the theories and analysis of how cell tissue responds to different oxygen levels and the benefits of EWOT, the reader is directed to Dr. Van Ardenne's publication entitled: "Oxygen Multi-Step Therapy: Physiological and Technical foundations", (1990, ISBN-13: 978-3137435013), which is considered a leading authority on the subject and is incorporated by reference herein in its entirety.

Through his research, Dr. Von Ardenne found that higher levels of oxygen in the body can contribute to the recovery of various ailments and diseases and help to achieve optimum overall health and longevity. For example, in some studies, Von Ardenne found that test subjects using EWOT improved their memory an average of 20%, and reaction times in certain activities an average of 15%.

The air reservoir 102 preferably includes physically separate first and second bladders 104, 106, although such quantity and configuration is not considered limiting as a single container can be provided which is partitioned by stitching, welding, a divider member and the like to form adjacent bladder sections (e.g., two bladders) in the container. In one aspect of the present invention, the first bladder 104 includes one or more weighted members 160 which apply a downward pressure on the first bladder 104 to help provide a positive pressure to the oxygen-enriched air that the user breathes when exercising, as discussed below in further detail. In an alternative embodiment, the first bladder 104 includes a plurality of folded pleats that unfold during the expansion of the first bladder 104, and then return to the biased, folded state as the air therein is depleted, such that the return of the pleats to their normal folded state causes a downward and positive pressure on the air content therein. Further details of the pleated bladder are discussed below with respect to FIG. 6.

Returning again to FIG. 1, the first bladder 104 includes an inlet port 112 which is coupled to an outlet port 113 of the air supply 120 via a first inlet air hose 114. Similarly, the second bladder 106 includes a second inlet port 115 which is coupled to a second outlet port 116 of the air supply 120 via a second inlet air hose 117. The first bladder 104 also includes an outlet port 118 which is coupled to a first inlet port 151 of the control switch 150 via a first outlet air hose 154. Similarly, the second bladder 106 includes a second outlet port 119 which is coupled to a second inlet port 152 of the control switch 150 via a second outlet air hose 155. The first inlet/outlet ports 112, 118 of the first bladder 104 are illustratively shown positioned at the top portion of the bladder 104, although such location is not considered limiting, as the first inlet/outlet ports 112, 118 can be positioned on the bottom, sidewall and/or other location depending on the shape of the first bladder 104. Similarly, the second inlet/outlet ports 115, 119 of the second bladder 106 are shown at opposing ends of the second bladder 106, although such positioning is not considered limiting, as the second inlet/outlet ports 115, 119 can be positioned on a sidewall and/or other location depending on the shape of the second bladder 106.

A person of ordinary skill in the art will appreciate that air flow directional-control devices 158, such as relief valves, check valves, flap valves/gates, and the like, can optionally be provided along the various air hoses, such as the first and second outlet air hoses 154, 155 to prevent backflow. The control switch 150 includes an outlet port 153 which is coupled to an inlet 132 of the breathing mask 130 via a third outlet air hose 156. The control switch 150 includes a actuator 155 that is either manually operated or programmed to operate automatically (as discussed below in further detail) to permit flow of the high or low (hypoxic) oxygenated air from the first bladder 104 or second bladder 106 to the breathing mask 130 so the user can breathe such selected air for a predetermined time.

The first and second bladders 104, 106 are preferably fabricated from a non-porous, durable material such as, for example, nylon fabric and the like, although such exterior surface materials are not considered limiting. The interior of the first and second bladders 104, 106 is preferably coated or lined with a non-toxic, medical-grade material or film which does not discharge or release chemical contaminants or pollutants into the stored air, such as thermoplastic polyurethane, Teflon, and the like. The bladder fabrication material(s) are selected to allow the bladders to easily expand and contract when the air is delivered into or released from the bladders, respectively, and a person of ordinary skill in the art will appreciate that the materials used to fabricate the first and second bladders 104, 106 are not considered limiting. Preferably, the seams of the bladders 104, 106 are joined together by RF welding or otherwise bonded together to ensure that the bladder seams will not leak.

The shape of the first bladder 104 is preferably cylindrical, although such shape is not considered limiting, as rectangular, triangular, octagonal, square or other shapes can be implemented. The cylindrical first bladder has circular top and bottom surfaces which are substantially planar, and a circular sidewall extending along a longitudinal axis "L" (e.g., see FIG. 6) between the top and bottom surfaces in a well-known manner. Preferably, the height-to-diameter ratio of the first cylindrical shaped bladder 104 is approximately 3:1, although such ratio is not considered limiting. The cylindrical shape of the first bladder 104 is advantageous for reducing the footprint of the EWOT apparatus, since the first bladder 104 can be positioned with its longitudinal axis oriented upward and remain vertically in a stable manner, i.e., without tilting or falling over. The cylindrical shape is also advantageous when the air is released from the first bladder 104, since the first bladder will collapse downwardly and uniformly from top to bottom, as discussed below in further detail with respect to FIGS. 2 and 6. The first bladder 104 is sized and dimensioned to retain a sufficient quantity of oxygen-enriched air (e.g., 93% oxygen) to last for a predetermined time, (e.g., fifteen minutes) when a user exercises and breathes through the mask 130 while using the portable oxygen supply 120. In one embodiment, the first bladder 104 has a volume of approximately 900 liters, although such volume is not considered limiting. The dimensions of the first and second bladder 104, 106 are generally determined in part by the type of the air supply 120 used in the EWOT system 100, but by no means are limited to just a cylindrical shape.

Commercially-available, portable air supplies 120 generally produce one concentration type of oxygen or the other, i.e., either the highly oxygenated air or the low (hypoxic) oxygenated air. In one embodiment, a first portable air supply 120 that is capable of producing oxygen-enriched air having 93% oxygen at a flow rate of 10 liters/min is provided for use in the EWOT system 100. As well, The EWOT system 100 can include a second portable hypoxic oxygen air supply which can produce a fixed low level of oxygen (hypoxic), e.g., an average 14% at a flow rate of 120 liters/min.

Figure 3:
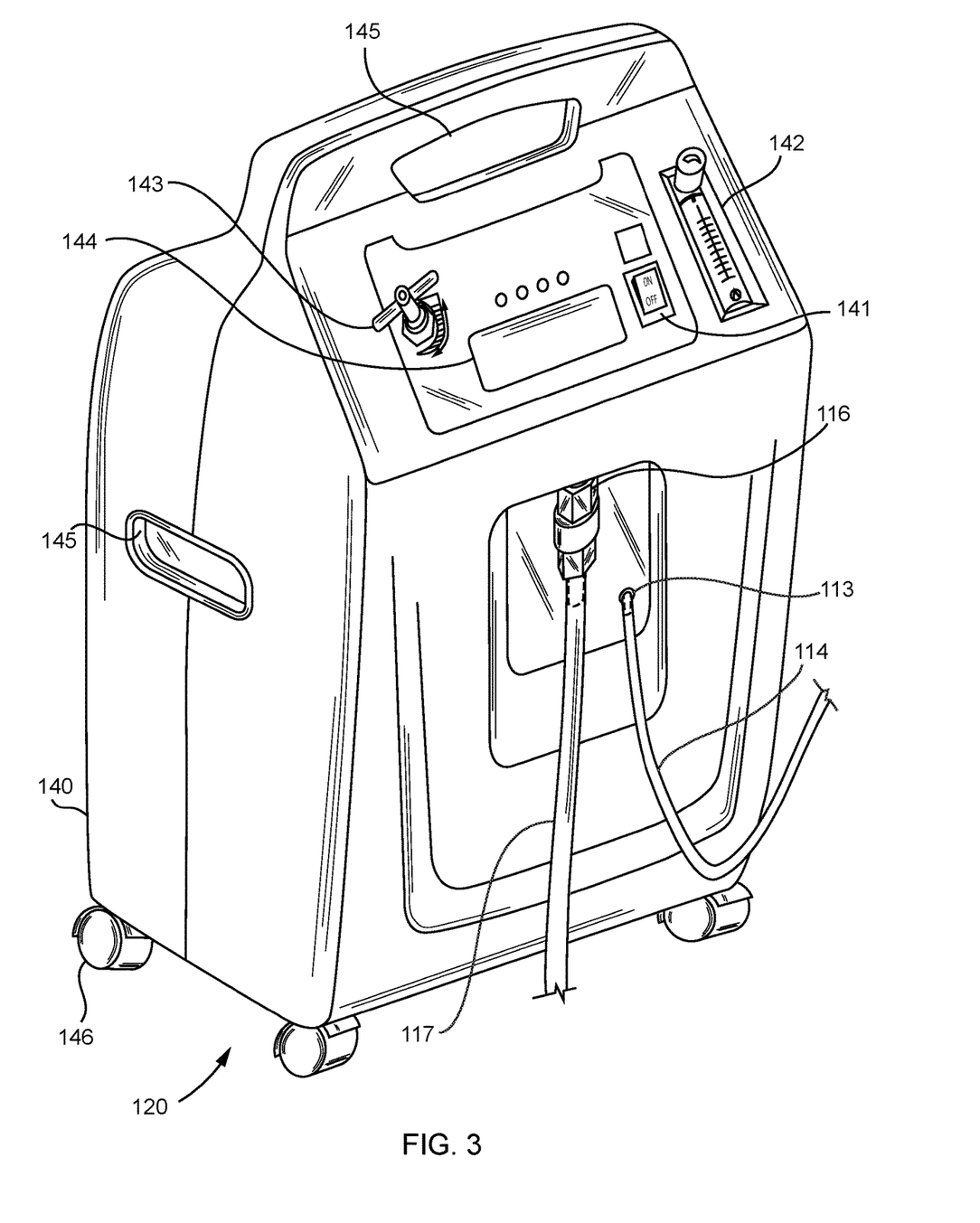
FIG. 3 is a top, front left-side perspective view of the air supply shown in FIG. 1.
Figures 4A, 4B, 4C:
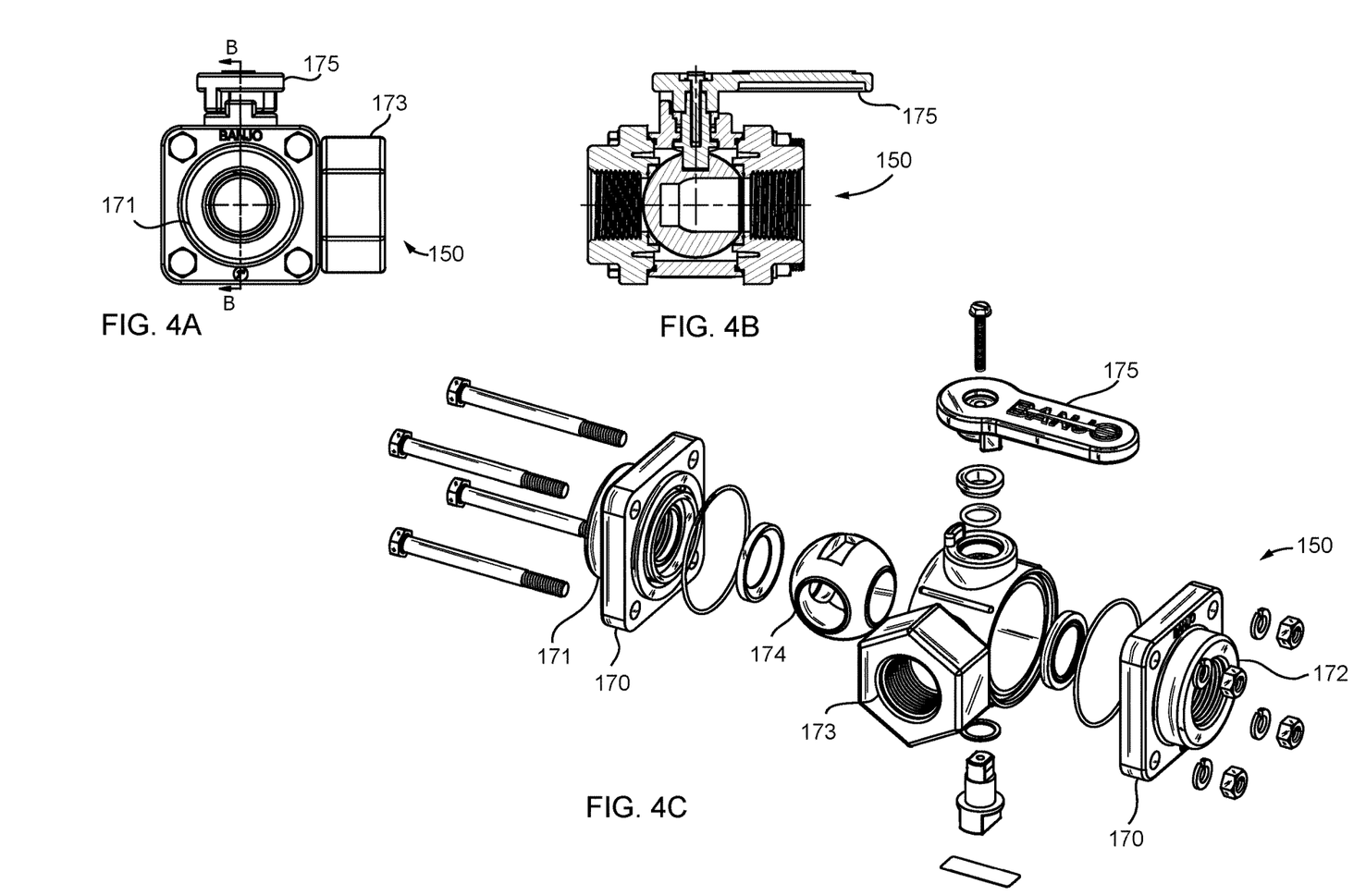
FIGS. 4A, 4B and 4C depict a left side elevation view, a front elevation view, and an exploded top, front, right-side perspective view, respectively, of a mechanical control switch suitable for mounting on the user's exercise device to manually control air flow from the first and second bladders of FIG. 1 to a user wearing a breathing mask.

Referring to FIG. 3, preferably, a portable air supply that can produce both the high concentration and a variable low concentration of oxygen (hypoxic) (e.g., from 8% to 20.95%) is implemented in the EWOT system 100, thereby eliminating the need and costs for two separate air supply units. The illustrative portable air supply 120 includes a housing 140 with one or more handles 145 and rollers (e.g., casters) to assist with transport of the air supply. The air supply 120 also includes an electric power switch 141 to turn the air supply on and off, a micro-interval altitude gauge 142 to indicate and finely adjust the simulated altitude level being produced, a macro-interval altitude gauge (e.g., rotatable handle) 143 to adjust the altitude simulated altitude range by, for example, thousands of feet, and a display panel 144 to display oxygen levels, simulated altitudes, directions, warnings, and other information to a user. A first outlet port 113 is provided, (e.g., extends from the housing 140) and configured such that a breathing tube 114 can be attached for coupling to and delivering highly oxygenated air to the first bladder 104. Similarly, a second outlet port 116 is also provided, (e.g., extends from the housing 140) and configured such that a second breathing tube 117 can be attached for coupling to and delivering hypoxic air the second bladder 106, as discussed below in further detail with respect to FIGS. 1 and 5.

Referring to FIGS. 1 and 3, a single portable air supply 120 is preferably connected to both the first and second bladders 104, 106 to separately and simultaneously pump the desired oxygen-enriched air and the hypoxic level air (e.g., 8% to 20.95%% oxygen) to the individual bladders. Although the use of a portable air supply 120 is desirable for a number of considerations, e.g., smaller footprint, mobility and purchasing cost outlays, there are presently limits with respect to the amount of high-level oxygen airflow rates that can be provided. Generally, it takes longer to produce and deliver the highly enriched oxygenated oxygen to fill the first bladder 104, as compared to the time to generate the lower hypoxic level oxygen. Because the high altitude hypoxic oxygen has a substantially lower concentration of oxygen as compared to the high concentrated oxygen, as well as the bladder size difference, the time to fill the smaller second bladder 106 is much less than the time required to fill the larger first bladder 104. Further, the portable air supplies do not have the oxygen generation capacity as compared to larger, stand-alone non-portable air supplies, or when configuring with other portable air supplies to operate in parallel to fill a bladder.

The manufacture-rated air flow rates of the air supply 120 and the desired time a user will exercise/breathe the high oxygenated air with the EWOT apparatus 100 are variables used to determine the required volume of the first bladder 104. In one embodiment where a commercially available portable air supply 120 is used in the EWOT system 100, the volume of the first bladder 104 is preferably approximately 700-1000 liters, and more preferably 900 liters to sustain a rigorous exercise routine for approximately fifteen minutes, as discussed below in further detail with respect to implementing a programmable controller for automatically controlling the exercise routines. Illustratively, the cylindrical-shaped first bladder 104 shown in FIG. 1 preferably has a diameter and height of approximately seventy-three (73) centimeters (cm) and two-hundred and thirteen (213) cm, respectively, which is approximately 900 liters. A person of ordinary skill in the art will appreciate that the volume of the first bladder 104 is not considered limiting as flow rates from other air supply manufacturers/models will influence the volume and dimensions of the first bladder 104.

The second bladder 106 has a volume that is significantly smaller than the first bladder 104, since a much lower concentration of hypoxic oxygen has to be generated and pumped into the second bladder. Thus, the second bladder 106 can be filled at a quicker flow rate. In the illustrative embodiment shown in FIG. 1, the second bladder 106 can have a volume in the range of 20-40 liters, and preferably a volume of approximately 30 liters. In one embodiment, the second bladder 106 is pillow-shaped having dimensions of approximately 30 cm×110 cm, although such volume size, shape and dimensions are not considered limiting for similar reasons discussed above with respect to the first bladder 104. Accordingly, it can take up to approximately 1.5 hours to fill the first bladder 104 with the high-level oxygenated air, and up to approximately 1 minute to fill the second bladder 106 with hypoxic air.

The frame 110 is preferably fabricated from a plurality of horizontal and vertical frame members 111 connected together in a rectangular shape to house and slidably support the first bladder 104. More specifically, the frame 110 illustratively includes four vertical frame members that are joined at opposing top and bottom ends by four horizontal frame members, although such configuration is not considered limiting. The frame members 111 are preferably tubular and can be formed from one or more durable and lightweight materials that are substantially rigid and can be easily assembled and transported without disassembly such as, for example, a metal/metal alloy (e.g., aluminum), polyvinyl chloride, polyethylene, and/or wood materials and the like. The horizontal and vertical frame members 111 can be secured together by fasteners (screws, spring loaded fasteners, etc.), snap-fit, adhesive, welding, bonding, among any other well-known fasteners.

Figure 2:
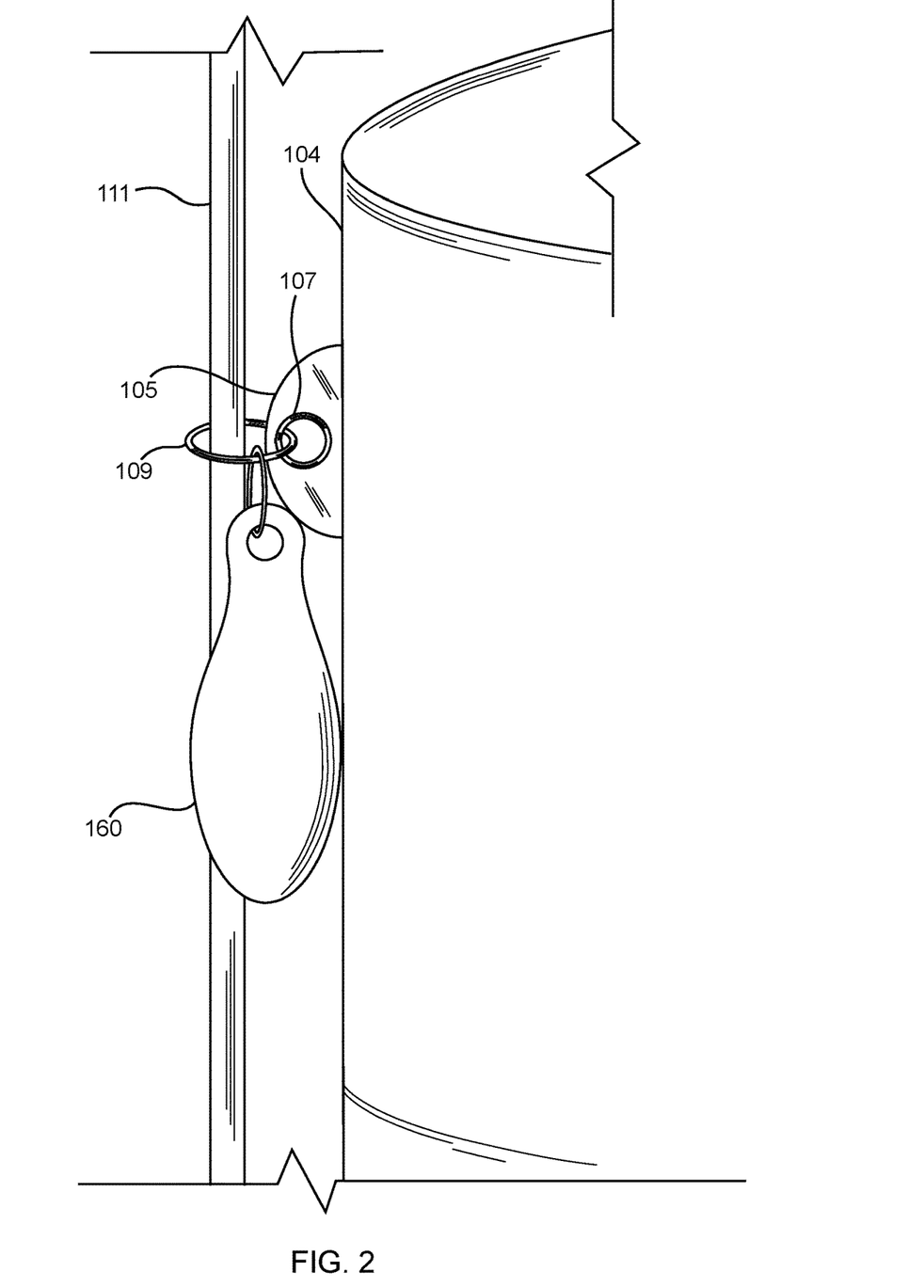
FIG. 2 is an exploded left-side elevational view of the support frame and first bladder slidably attached thereto as shown in FIG. 1 illustrating an embodiment of a weighted member for applying a downward force to induce a positive air pressure inside the first bladder.

Referring to FIGS. 1 and 2, the height and width of the frame 110 are greater than the height and width (diameter) of the cylindrical-shaped first bladder 104 when inflated to avoid interference and/or kinking therewith. The first bladder 104 includes a plurality of tabs 105 each having an aperture that is preferably formed by a grommet 107 (e.g., brass or plastic grommet) for attachment to the vertical frame members 111 via a ring 109. The rings 109 are sized to easily slide up and down the vertical frame members 111 and in one embodiment, the rings 109 have a diameter of two inches, although such dimension is not considered limiting. The first bladder 104 illustratively includes four sets (three sets shown in FIG. 1) of three vertically-aligned tabs/grommets 105,107 that are spaced apart along the top, middle and bottom length of the cylindrical first bladder 104. The four sets of vertically-aligned tabs/grommets 105, 107 are evenly spaced around the outer circumference of the cylindrical first bladder 104 and are aligned adjacent to one of the four vertical frame members 111. The tabs/grommets/ring 105, 107, 109 arrangement slidably secures the first bladder 104 to the vertical frame members 111 in opposing horizontal directions so that the width or diameter of the first bladder 104 is always maintained in a generally expanded state. When the first bladder 104 is devoid of air, the top portion of the first bladder 104 is collapsed and the top of the bladder and the aligned sets of tabs/grommets/rings are positioned proximate the bottom of the frame 110. When the oxygen-enriched air is supplied to the first bladder 104 by the air supply 120, the incoming air pressure (ambient air pressure) expands and fills the first bladder 104 in an upward vertical direction. The tabs and rings 105/107 slidably guide the expanding first bladder 104 upwardly within the frame 110 until fully expanded. The arrangement of tabs 105 and rings 109 prevent the first bladder 104 from twisting or getting kinked in the frame 110 while rising when being inflated with air or descending along the vertical frame members when air is depleted during use.

As noted above, one or more weighted members 160 can be attached to the first bladder 104. The weighted member(s) have sufficient weight to apply a downward positive pressure force on the first bladder 104 when filled with air, such that a constant, positive pressure is applied to the air stored within the first bladder 104 so as to provide steady and sufficient airflow to the user while breathing through the mask 130 when exercising. That is, the positive pressure applied to the air within the first bladder 104 provides an increased flow rate of the oxygen-enriched air to the mask 130, to thereby deliver an uninterrupted and plentiful supply of air to the user while exercising, as compared to the prior art systems which utilize ambient-pressure oxygen levels.

Preferably, a plurality of weighted members 160 are attached to an upper portion of the first bladder 104 via the rings 109 and/or grommets 107, and thereby hang downward to help collapse the first bladder 104 in a vertical direction when the user breathes the stored air during use. The weighted members 160 are preferably uniform in shape and weight so as not to interfere with the slidable vertical movement of the rings 109 as the first bladder 104 moves up and down the along the frame 110. The weighted members 160 can be fabricated from a durable material such as metal (e.g., stainless steel), ceramic (e.g., plastic filled with sand) or any other well-known durable material or combination thereof. Illustratively, the total weight of the weighted members 160 for a 900 liter cylindrical bladder is approximately 1.8 kg, although such weight is not considered limiting, as a person of ordinary skill in the art will appreciate that the volume of the first bladder 104 and the flow rate of high oxygenated air from the air supply 120 are determining factors of the total weight to be implemented. The plurality of weights 160 are preferably evenly distributed around the upper tabs 105 of the first bladder 104, although such positioning is not considered limiting. For example, two sets of weights 160 can be provided along each vertical frame member at the upper and middle tabs. Alternatively, all three vertically aligned tabs can include a weighted member 160 at each vertical frame member 111. A person of ordinary skill in the art will appreciate that the type, arrangement, sizes, quantity, weighting and positioning of the weight members 160 as discussed herein and shown in FIG. 1 is not considered limiting. For example, a single or set of weighted members 160 can be attached (e.g., bonded, stitched, welded and the like) to the upper top surface of the first bladder 104. Alternatively, the weighted members 160 can be attached to the sidewall(s) of the first bladder 104 instead of being hung from the tabs 105. In any of the embodiments for providing one or more weighted members 160, the weighted member(s) 160 apply a downward pressure on the first bladder 104, thereby providing a positive pressure on the stored air. The positive pressure from the first bladder 104 is beneficial to the user during an exercise routine, since the user will receive an increased and unencumbered steady flow of the oxygen-enriched air when breathing harder and faster through the mask 130.

Referring again to FIG. 1, the second bladder 106 is much smaller than the first bladder 104, since the production of the low concentration of oxygen takes much less time than the production of highly oxygenated air. The smaller second bladder 106 is illustratively mounted on the top horizontal members 111 of the frame 110. Alternatively, the second bladder 106 can be hung with a fastener such as an S-hook, carabiner or other clip/fastener from one of the horizontal members 111. The second bladder 106 can also be positioned and secured beneath the first bladder 106. The first and second bladders 104, 106 preferably include a relief valve 121 or 158 (e.g., flap valve, bleeder valve and the like) to prevent overfilling of air from the air supply 120. Each relief valve 121 is normally in a closed state and will open when the pressure inside a bladder exceeds a predetermined pressure to thereby allow excess air to escape into the surrounding environment. In one embodiment, the relief valves 121 or 158 associated with the second bladder 106 will open when, for example, the hypoxic oxygen inside the second bladder 106 exceeds full capacity, e.g., 30 liters. Similarly, air from the first bladder 104 can be released via the corresponding relief valves if the air capacity of the first bladder 104 is exceeded. The breathing mask 130 can also include a relief valve (not shown) in a well-known manner.

Figure 6:
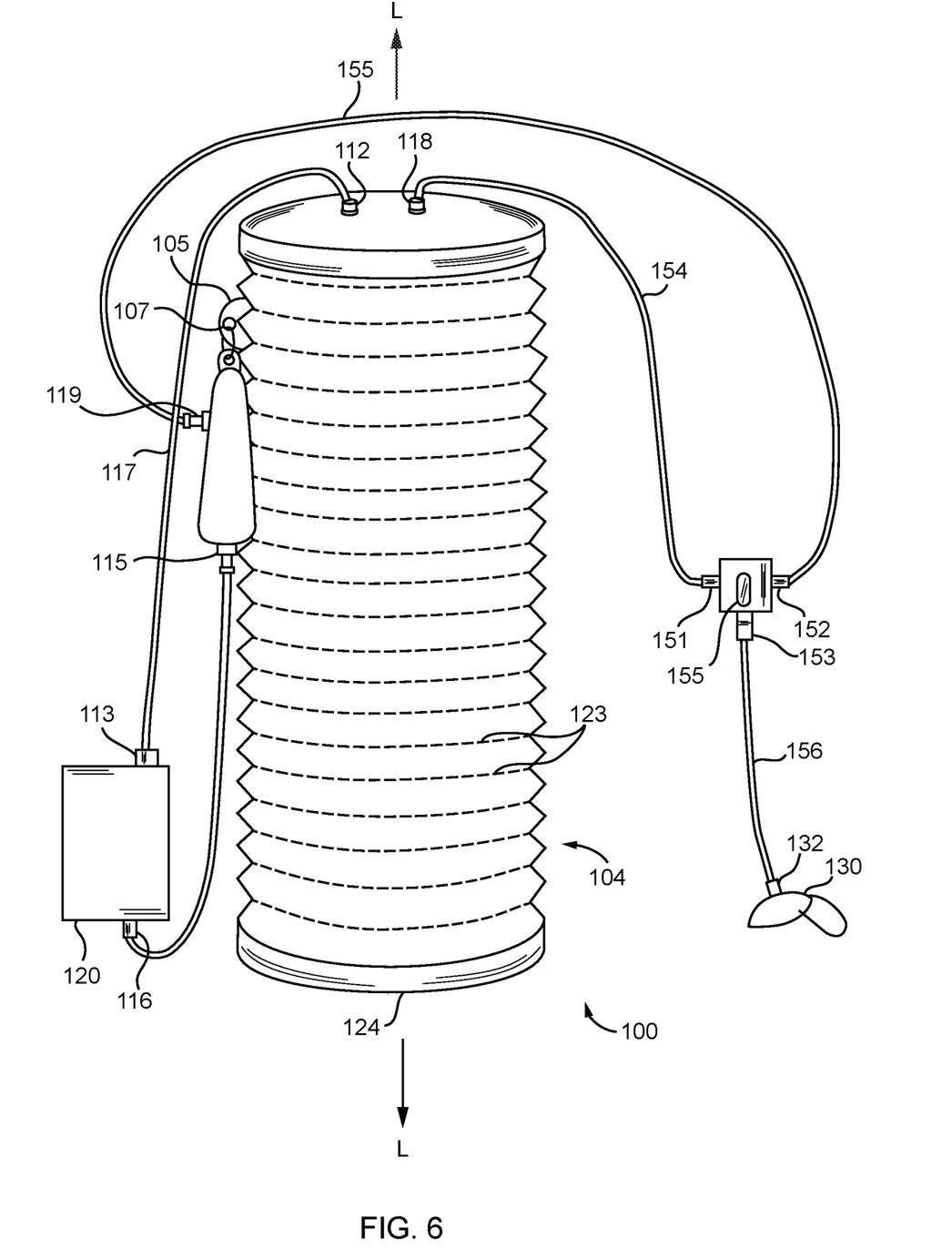
FIG. 6 is a top, front, right-side perspective view of yet another embodiment of the EWOT training device and illustrating another embodiment of the first inflatable bladder.

Referring now to FIG. 6, another embodiment of the EWOT system 100 is shown. The illustrative embodiment of FIG. 6 is similar to the previous embodiment shown in FIG. 1, except that the first bladder 104 includes a plurality of pleats (i.e., creases and folds) 123 formed concentrically on and orientated horizontally around the sidewall of the first bladder 106 to thereby enable the bladder 106 expand and collapse in a vertical direction in a similar manner as a bellows or accordion expands/contracts when the air is respectively pumped into or released therefrom. The pleats 123 are preferably biased in folded state and unfold and expand when air is injected into the first bladder 104, and collapse (i.e., fold up) to return to their normally-biased, folded state when air is released from the first bladder 104. Although the pleated first bladder 104 is shown as a cylindrical shaped bladder in FIG. 6, such shape is not considered limiting, as other shapes, such as rectangular, triangular, square, octagonal, frusto-conical, among other well-known or customized shapes can be implemented.

In one embodiment, the pleated sidewall 123 of the first bladder 104 is sufficiently rigid enough to enable the bladder to retain a stable, upright position when filled with air such that the EWOT system 100 can be used without the inclusion of the frame 110. That is, the pleated sidewall 123 supports the first bladder 104 in an expanded and vertical orientation without tilting or falling over, even during the expansion or the downward collapse of the bladder while increasing/decreasing the internal air volume. In lieu of the frame 110 (i.e., the absence thereof), additional stability can be provided by including a weighted member 124 at the bottom portion of the pleated bladder 104 to help maintain the bladder 104 in a stable, upright position. The weighted member 124 can be a mixture of sand, metal/metal alloys and/or other weighted material that will assist in maintaining bladder 104 in a vertical orientation relative to the floor surface when expanding or collapsing. For example, in one embodiment the weighted member 124 is a layer of sand that is dispersed substantially over the interior bottom surface of the bladder. Alternatively, the weighed member 124 is ring that is positioned along the periphery of the bottom surface. The pleated sidewall(s) 123 is preferably configured or fabricated such that a downward pressure is always exhibited on the air volume therein, such that a positive pressure is created on the high-level oxygen when the user is exercising. In this manner, the weights 160 can optionally be provided or preferably eliminated completely from the EWOT system 100. The second bladder 106 can be hung from a grommet 107 in a similar manner as discussed above with respect to FIG. 2 (i.e., in place of or adjacent to a weight 160), or rest on the floor adjacent to the first bladder 104, the pump 120 or in a non-intrusive location elsewhere.

The control switch 150 controls the airflow from the first and second bladders 104, 106 to the breathing mask 130 so that the user can selectively breathe the oxygen-enriched or lower purity hypoxic air for predetermined periods of time while exercising. Referring to FIGS. 1 and 4A-4C, a manually operated control switch 150 includes a housing 170 having a first inlet 171, a second inlet 172, an outlet 173, a control valve 174, and an actuator 175. Preferably, the control valve 174 is a ball valve with a handle (actuator) that can be manually rotated to allow the selected air to flow from first bladder 104 or the second bladder 106 to the mask 130 when desired by the user or at predetermined times. The control switch 150 is preferably mounted to the users' exercise equipment at a convenient location so that the user can easily access and activate/deactivate the control switch 150, although such location is not considered limiting. Although a ball valve having two inlets and a single outlet is illustratively shown in FIGS. 4A-4C, a person of ordinary skill in the art will appreciate that other electro-mechanical airflow controllers can be utilized, such as slidable control valves, solenoid-controlled valves, or any other commercially available valve that can quickly change airflow supplied from either or both of the first and second bladders 104, 106. In another embodiment, the control switch 150 is programmable to automatically switch airflow delivered from the first and second bladders 104, 106 to the mask 130.

Figure 5:
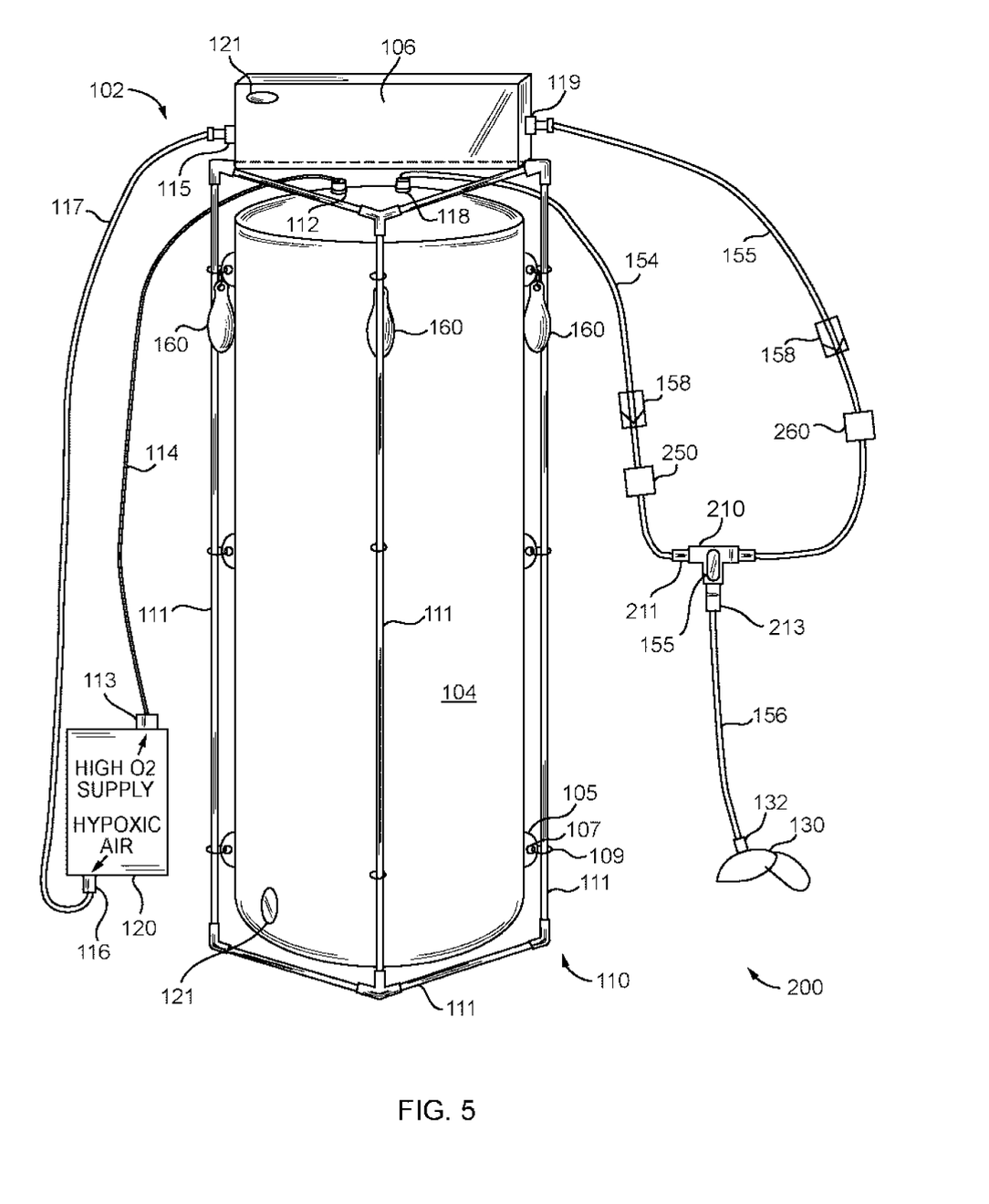
FIG. 5 is a top, front, right-side perspective view of the EWOT training device of FIG. 1 having multiple airflow control switches in accordance with another embodiment of the present invention.
Figure 7:
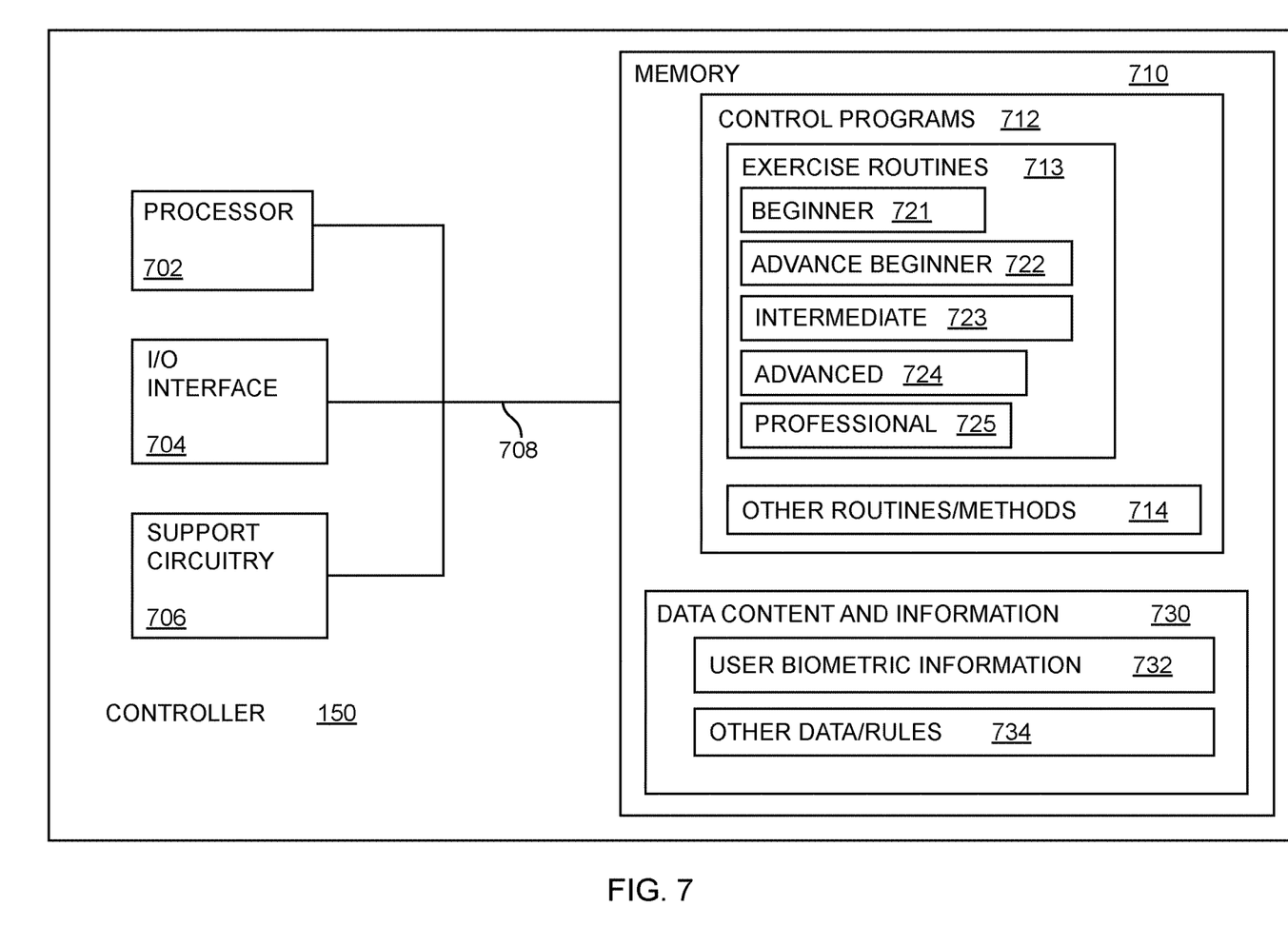
FIG. 7 is a functional block diagram of a programmable controller suitable for controlling air flow in the EWOT training devices of FIGS. 1, 5 and 6.

Referring now to FIG. 7, a functional block diagram of a programmable controller 150 that is suitable for automatically controlling air flow in an EWOT training device 100 such as the EWOT devices of FIGS. 1, 5 and 6 is illustratively shown. The controller 150 illustratively comprises a processor 702 as well as memory 710 for storing various control programs 712 and data 730. The processor 702 is preferably a microcontroller, but can be any conventional processor, such as one or more central processing units, e.g., an Intel microprocessor(s). The memory 710 can illustratively be partitioned to store control programs 712 apart from data content and information 730, although such memory arrangement is not considered limiting. The memory 710 can comprise volatile memory (e.g., erasable Flash memory, RAM, etc.), non-volatile memory (e.g., solid state drives) and/or a combination thereof. The microprocessor 702 cooperates with the memory 710 and support circuitry 706, such as power supplies, clock circuits, cache memory, memory controllers, graphic controllers, bus controllers, input/output (I/O) controllers, GPS circuitry, among other conventional support circuitry via electronic communication paths (buses) 708, to assist in transferring data 730 and executing software routines (e.g., exercise routines 713) stored in the memory 710.

As such, it is contemplated that some of the process steps discussed herein as software processes can be implemented within hardware, for example, as circuitry that cooperates with the microcontroller/processor 702 to perform various steps. It is noted that an operating system (not shown) and optionally other various application programs 714 can be stored in the memory 710 to run specific tasks and enable user interaction. The controller 150 also comprises input/output (I/O) circuitry 704 that forms an interface between various functional elements communicating with the controller 150. For example, one or more sensors can be in electronic communication with the I/O interface 704 to provide biometric readings from a user that is exercising with the EWOT apparatus 100. The biometric readings such as oxygen levels, temperature, blood pressure and heart rate from the sensors received by the controller 150 can be compared by the processor 702 with biometric information 732 of the user and/or other data 734 (e.g., biometric norms and statistics) that are stored in the memory 732 to maintain, terminate or deviate from the current running exercise routine 713.

Although the controller 150 of FIG. 7 is depicted as a general-purpose computer that is programmed to perform various defined and/or control functions for specific purposes in accordance with the present invention, the invention can be implemented in hardware such as, for example, an application specific integrated circuit (ASIC). As such, it is intended that the processes described herein be broadly interpreted as being equivalently performed by software, hardware, or a combination thereof. Furthermore, although the exemplary controller 150 is shown as a single controller unit, a person or ordinary skill in the art for which the present invention pertains will appreciate that a plurality of controllers can be implemented in the EWOT apparatus 100 to control the air flow and exercise routines, as illustratively discussed below with respect to FIG. 5. In such embodiment, the plurality of controllers can be organized as a network of controllers, including wireless and Bluetooth devices, to provide alternative and/or shared control of the EWOT training apparatus 100 during an exercise routine.

Illustratively, one or more exercise training routines 713 (e.g., interval training routines) can be programmed into the microcontroller 702 to provide automatic switching of the high and low (hypoxic) oxygen levels of airflow from the first and second bladders 104, 106. In one embodiment, the microcontroller 702 is preprogrammed to monitor/store in its memory 710 the current time, an exercise start time, a predetermined duration of exercise, a number of and duration for interval or random air flow switching times to occur during the exercise routine. Accordingly, the user can select a suitable program 713 that will result in the delivery of either the highly oxygenated and/or variable low (hypoxic) oxygenated air to breathe for predetermined times during the exercise routine. A person skilled in the art will appreciate that other metrics and programming (e.g., alarms) can be included, that further assist the user during the exercise routine. For example, in another embodiment, biometric information 732 about the user (height, weight, age and the like) can also be stored in memory 730 and provided to the microcontroller 702 when running one of the exercise routines 713. Although the present embodiment is discussed using a microcontroller for controlling the controller(s) 150, a person of ordinary skill in the art will appreciate that other control circuits, such as a microprocessor with external memory, programmable logic circuitry (PLC) and the like can be utilized.

In one illustrative embodiment, the controller 150 is pre-programmed by the manufacturer to execute or run a variety of exercise programs 713 having different levels of endurance strengthening including, for example, "Beginner" 721, "Advanced Beginner" 722, "Intermediate" 723, "Advanced" 724, and "Professional" 725 levels. Alternatively, the controller 150 can have manual settings or be custom programmed by the user. Examples of the pre-programmed endurance strengthening routines include, but are not limited to:

Beginner Level 721—15 minutes of High Purity 93% Oxygen.

Advanced Beginner 722—5 minutes of High Purity 93% Oxygen; 1 minute of Low Purity Hypoxic that can be user adjusted between 8% to 20.95% Oxygen; 2 minutes of High Purity 93% Oxygen; 1 minute of Low Purity Hypoxic that can be user adjusted between 8% to 20.95% Oxygen; 2 minutes of High Purity 93% Oxygen; 1 minute of Low Purity Hypoxic that can be user adjusted between 8% to 20.95% Oxygen; and 3 minutes of High Purity 93% Oxygen.

Intermediate Level 723—5 minutes of High Purity 93% Oxygen; 1 minute of Low Purity Hypoxic that can be user adjusted between 8% to 20.95% Oxygen; 1 minute of High Purity 93% Oxygen; 1 minute of Low Purity Hypoxic that can be user adjusted between 8% to 20.95% Oxygen; 1 minute of High Purity 93% Oxygen; 1 minute of Low Purity Hypoxic that can be user adjusted between 8% to 20.95% Oxygen; 1 minute of High Purity 93% Oxygen; 1 minutes of Low Purity Hypoxic that can be user adjusted between 8% to 20.95% Oxygen; and 3 minutes of High Purity 93% Oxygen.

Advanced Level 724—5 minutes of High Purity 93% Oxygen; 2 minutes of Low Purity Hypoxic that can be user adjusted between 8% to 20.95% Oxygen; 2 minutes of High Purity 93% Oxygen; 2 minutes of Low Purity Hypoxic that can be user adjusted between 8% to 20.95% Oxygen; 2 minutes of High Purity 93% Oxygen; 2 minutes of Low Purity Hypoxic that can be user adjusted between 8% to 20.95% Oxygen; and 2 minutes of High Purity 93% Oxygen.

Professional Level 725—5 minutes of High Purity 93% Oxygen; 2 minutes of Low Purity Hypoxic that can be user adjusted between 8% to 20.95% Oxygen; 1 minute of High Purity 93% Oxygen; 2 minutes of Low Purity Hypoxic that can be user adjusted between 8% to 20.95% Oxygen; 1 minute of High Purity 93% Oxygen; 2 minutes of Low Purity Hypoxic that can be user adjusted between 8% to 20.95% Oxygen; and 2 minutes of High Purity 93% Oxygen.

A person of ordinary skill in the art will appreciate that the types of programs and routines discussed herein are for illustrative purposes only and are not considered limiting.

As noted above, one or more biometric sensors can be placed in contact with the user while engaged in an exercise routine 713 to provide electronic signals to the microcontroller 702 to record the effects on, for example, pulse, heart rate, body temperature and the like. The microcontroller 702 can use the information from the sensor(s) as feedback and is preferably programmed to execute one or more commands that adjust the selected training routine program as required. For example, if the microcontroller 702 receives electronic signals indicating higher than normal blood pressure, temperature levels, oxygen levels, heart rate, and respiratory levels before a predetermined time lapses during a high altitude training routine in which hypoxic air is being delivered to the user, the airflow control switch 150 can illustratively change the duration that the user receives the lower purity (hypoxic) air to a shorter period and/or provide the oxygen-enriched air to help the user complete the exercise routine.

Referring now to FIG. 5, a second embodiment of the EWOT training device 200 is illustratively shown. The EWOT training device 200 is the same as the EWOT training device 100 as discussed with respect to FIG. 1, except that two electronic control switches 250 and 260 are provided to separately deliver the retained air from the first and second bladders 104, 106. In particular, the EWOT training device 200 includes the first and second bladders 104, 106 supported by the frame 110, the air supply 120, and the mask 130 as discussed above. The first control switch 250 is coupled between the outlet port 118 of the first bladder 104 and a first inlet 211 of a T-shaped connector 210 via air hose 154. Similarly, the second control switch 260 is coupled between the outlet port 119 of the second bladder 104 and a second inlet 212 of the T-shaped connector 210 via air hose 155. An outlet 213 of the T-shaped connector 210 is coupled to the inlet 132 of the breathing mask 130 via air hose 156. Air flow directional-control devices 158 can be provided along the air hoses 154, 155 to prevent backflow as discussed above with respect to FIG. 1. The control switches 250 and 260 are in electronic communication with each other via a wireless network and/or by hardwire. One of the control switches (e.g., switch 250) is normally in an open state, while the other control switch (e.g., switch 260) is normally in a closed state. In this manner, air from only one of the bladders 104, 106 can be delivered to the breathing mask 130 during an exercise routine. Alternatively, both of the electronic airflow controllers 250, 260 can be in and open state, i.e., fully or partially opened, to provide a predetermined mixture of air from the bladders to the user.

In yet another embodiment, a third control switch (not shown) can be coupled to the T-connector 210 and be in electronic communications with the other control switches 250, 260 to allow one or more auxiliary gasses such as, e.g., ambient air, nitrogen and the like to be delivered directly to the breathing mask 130 or mixed with one or both airflows from the bladders 104, 106 or an additionally added bladder prior to passage to the breathing mask 130.

The present embodiments of the EWOT apparatus 100 advantageously overcome the deficiencies of the prior art in numerous and beneficial manners. The various embodiments of the exercise with oxygen therapy (EWOT) apparatus 100, 200 of the present invention provide a high concentration of oxygen and a low concentration of oxygen relative to ambient air at sea level, and enables the user to selectively control the high and low oxygen air flows to breathe while exercising. The EWOT apparatus includes a pair of bladders, a first bladder for storing and delivering the high level of oxygen (e.g., 93%) and a second bladder for storing and delivering the low pressure adjustable oxygen air flow (e.g., 8%-20.95%) to the user. Breathing the low (hypoxic) oxygen level for a predetermined duration(s) while exercising can simulate training at high altitudes, and help the user better adapt to such conditions. This happens because the body's microvessels and capillaries open wide, or vasodilate, as the body starves itself of oxygen. By then breathing the high oxygen level air immediately while still exercising enables a user to replenish oxygen-deprived cell tissues and thereby permit the user to exercise longer, build higher immunity, gain energy and/or expediate recovery.

In one embodiment, a cylindrical-shaped first bladder is preferably used to provide a constant flow of the oxygen-enriched air to the user. The cylindrical shape bladder is oriented upright to thereby reduce the footprint of the EWOT apparatus as compared to other prior art EWOT systems. The cylindrical shape advantageously prevents undesirable twisting and kinking of the bladder when descending from a full upright position to an air-depleted, collapsed position at the bottom of the frame. The frame 110 in combination with one or more rings 109 advantageously helps guide the first bladder 104 up and down, and also prevents the bladder from falling laterally and out of the frame in what could become a potentially hazardous situation. In another beneficial aspect, the lightweight frame and inflatable/deflatable bladders, along with the single, portable air supply afford enhanced portability/mobility, thereby allowing the EWOT apparatus to be easily moved and transported.

A further enhancement can be seen by applying a positive pressure to the ambient air in the bladder with the assistance of one or more weighted members that help force the air out of the bladder. In one embodiment, one or more weights are positioned on or about the first bladder to produce a downwardly directed force on the air therein, which in turn provides a positive pressure as the oxygen-enriched air is being delivered from the bladder to the breathing mask of the user. Alternatively, the first bladder can include a plurality of folded pleats which expand when the first bladder is filled with air from the air supply. Preferably, the pleats are biased to return to their folded state as the air is depleted from the bladder, thereby applying a positive pressure to the air contained therein. Additionally, the cylindrical pleated bladder expands upwardly and contracts downwardly in a vertical direction without being prone to tilt or fall over, thereby optionally eliminating the need for the frame. In any of the embodiments, a positive pressure that is provided to the oxygen-enriched air enables the user to receive a steady and plentiful flow of the oxygenated air from the first bladder.

Additional embodiments and advantages include applying a coating of medical grade thermoplastic polyurethane, Teflon and the like to the interior walls of the first and second bladders to prevent oxygen contamination. The first and second bladders are carefully RF welded to prevent leakage. A single portable air supply can fill both bladders with the desired oxygen levels, for example, the first bladder can be filled with air that is 93% oxygen and the second bladder can be filled with air having a variable low range of oxygen such as, for example, between 8-20.95% oxygen. In this manner, the apparatus is capable of simulating oxygen levels of altitudes up to 21,000 feet to satisfy users who which to conduct intensive athletic training or health benefits.

Other advantages include a control switch (controller) which can include a microcontroller to store and execute programs which, when executed, enable the user to automatically switch between the oxygen-enriched air and low hypoxic oxygen level air stored in the bladders to better maximize breathing and performance while exercising and training. Further enhancements during exercise and training can be realized by using electronic biometric sensors that provide biometric feedback to the control switch, which can then make adjustments to the current training routine in response to the sensor information received.

Although the present invention has been shown and described with reference to a preferred embodiment, such is merely illustrative of the present invention and is not to be construed as limiting and various modifications of the present invention will be apparent to those skilled in the art. The scope of the present invention is therefore to be determined by the claims.

The invention claimed is:

1. A therapeutic oxygen breathing apparatus comprising:
    an air reservoir having a first bladder and a second bladder, the first and second bladders being configured for storing air having different percentages of oxygen therein;
    a frame structure configured to support at least the first bladder in a vertical direction;
    a weighted member attached to and positioned proximate an upper portion of the first bladder, the weighted member having sufficient weight to apply a downward force on the first bladder when filled with air, such that a constant, predetermined positive pressure is applied to the air stored within the first bladder;
    wherein the first bladder includes a first inlet for receiving a first quantity of air having a first concentration of oxygen and the second bladder includes a second inlet for receiving a second quantity of air having a second concentration of oxygen; and
    wherein the first bladder includes a first outlet for releasing a first portion of stored air having the first concentration of oxygen and the second bladder includes a second outlet for releasing a second portion of stored air having the second concentration of oxygen, and wherein the first concentration of oxygen is supplied from an external source and is greater than ambient air concentration of oxygen.

2. The therapeutic oxygen breathing apparatus of claim 1, wherein the first and second bladders are physically separated.

3. The therapeutic oxygen breathing apparatus of claim 1, wherein the second bladder is attached to the first bladder.

4. The therapeutic oxygen breathing apparatus of claim 1, wherein the first and second outlets are coupled to one or more airflow paths to a user, said one or more airflow paths being configured to occlude flow of air from the user to the first and second chambers.

5. The therapeutic oxygen breathing apparatus of claim 4, wherein the first concentration of oxygen is greater than ninety percent.

6. The therapeutic oxygen breathing apparatus of claim 4, wherein the second concentration of oxygen is supplied from an external source and is less than ambient air concentration of oxygen.

7. The therapeutic oxygen breathing apparatus of claim 6, wherein the second concentration of oxygen is between 8% to 20.95%.

8. The therapeutic oxygen breathing apparatus of claim 1, wherein the first bladder is cylindrical.

9. The therapeutic oxygen breathing apparatus of claim 1, wherein the frame includes a plurality of vertical and horizontal frame members collectively arranged in a rectangular shape, wherein the frame has a height-to-width ratio greater than one.

10. The therapeutic oxygen breathing apparatus of claim 9, wherein the first bladder is positioned within the rectangular frame in a vertical direction and slidably attached to the vertical frame members.

11. The therapeutic oxygen breathing apparatus of claim 10, wherein the first bladder is attached to the vertical frame members via a plurality of rings.

12. The therapeutic oxygen breathing apparatus of claim 10, wherein the weighted member is attached to an exterior portion of the first bladder and slidably moves along one of the vertical frame members.

13. The therapeutic oxygen breathing apparatus of claim 1, wherein the weighted member is positioned on an upper surface portion of the first bladder.

14. The therapeutic oxygen breathing apparatus of claim 1, wherein the first outlet is in fluid communication with a first airflow directional valve that permits unidirectional airflow out of the first bladder.

15. The therapeutic oxygen breathing apparatus of claim 1, wherein the second outlet is in fluid communication with a second airflow directional valve that permits unidirectional airflow of air out of the second bladder.

16. The therapeutic oxygen breathing apparatus of claim 11, wherein the second bladder is attached to the frame.

17. The therapeutic oxygen breathing apparatus of claim 1, further comprising a breathing mask having an inlet which is coupled to the first and second bladders via a control switch.

18. The therapeutic oxygen breathing apparatus of claim 17, wherein the control switch is in fluid communication with the first and second outlets of the first and second bladders.

19. The therapeutic oxygen breathing apparatus of claim 17, wherein the control switch includes a valve and an actuator for manually selecting airflow from at least one of the first and second bladders to the breathing mask.

20. The therapeutic oxygen breathing apparatus of claim 17, wherein the control switch incudes a programmable microcontroller for executing routines which automatically control a valve to selectively permit air to flow from at least one of the first and second bladders to the breathing mask.

21. The therapeutic oxygen breathing apparatus of claim 20, wherein the control switch is configured to receive electronic signals from one or more biometric sensors in communication with a user wearing the breathing mask.

22. The therapeutic oxygen breathing apparatus of claim 21, wherein the control switch includes programming that sends electronic signals to actuate the valve which adjusts, in real time, air flow from at least one of the first and second bladders, in response to the electronic signals from the one or more biometric sensors.

23. The therapeutic oxygen breathing apparatus of claim 17, wherein the control switch includes a first control switch for receiving airflow from the first bladder and a second control switch for receiving airflow from the second bladder.

24. The therapeutic oxygen breathing apparatus of claim 23, wherein the first and second control switches are in electronic communication with each other.

25. A dual bladder system for supplying gasses while exercising, comprising:
a cylindrical inflatable and collapsible first bladder dimensioned and configured to receive and store a first gas having a first concentration of oxygen via a first inlet, the first bladder being biased towards a collapsed state and postioned in an external ambient pressure environment, wherein the first concentration of oxygen is supplied from an external source and is greater than ambient air concentration of oxygen;
a second bladder dimensioned and configured to receive and store a second gas having a second concentration of oxygen via a second inlet;
a mixer coupled to the first and second bladders, the mixer having an actuator for selectively providing at least one of the first and second gases to a user;
wherein the first bladder includes a first outlet for releasing a first portion of the stored first gas and the second bladder includes a second outlet for releasing a second portion of the stored second gas; and
wherein the first and second outlets are coupled to one or more airflow paths to the user, said one or more airflow paths being configured to occlude backflow of air from the user to the first and second chambers.

26. The dual bladder system of claim 25 further comprising a frame structure configured to support at least the first bladder in a vertical direction.

27. The dual bladder system of claim 25, wherein the first bladder is pleated such that the pleats unfold to permit the first bladder to expand during receipt of the first gas.

28. The dual bladder system of claim 27, wherein the pleats are biased to return to a folded state and collapse the first bladder in a vertical direction as the first gas is depleted from the first bladder.

* * * * *